United States Patent [19]

Chao

[11] Patent Number: 5,185,160

[45] Date of Patent: Feb. 9, 1993

[54] PLATELET MEMBRANE MICROVESICLES

[75] Inventor: Francis C. Chao, Newton, Mass.

[73] Assignee: PRP, Inc., Watertown, Mass.

[21] Appl. No.: 337,916

[22] Filed: Apr. 14, 1989

Related U.S. Application Data

[63] Continuation-in-part of Ser. No. 73,102, Jul. 14, 1987, abandoned, which is a continuation-in-part of Ser. No. 623,074, Jun. 21, 1984, abandoned.

[51] Int. Cl.$^5$ ........................ A61K 35/14; C12N 7/04
[52] U.S. Cl. .................................... 424/532; 435/236
[58] Field of Search ................. 424/101, 532; 435/236

[56] References Cited

U.S. PATENT DOCUMENTS

| | | | |
|---|---|---|---|
| 4,456,590 | 6/1984 | Rubinstein | 424/530 |
| 4,540,573 | 9/1985 | Neurath et al. | 424/101 |
| 4,753,797 | 6/1988 | Garcez | 424/530 |
| 4,760,131 | 7/1988 | Sundomo et al. | 424/101 |
| 4,764,463 | 8/1988 | Mason et al. | 424/101 |
| 4,994,438 | 2/1991 | Rubinstein | 424/530 |

OTHER PUBLICATIONS

George et al., Biol. Abstracts, vol. 82:69920 (1986).
McGill et al., Transfusion Abstract (1983) p. 414.
McGill et al., J. Lab. Clin. Med. 109:127 (1987).
Klein et al., Am. J. Pediat. 49:517 (1956).
Alkjaersig et al., Am. J. Physiol. 1810, 304–307 (1955).
Wu et al., Thromb. Res. 11:581 (1977).
Sandberg et al., Biochem. J. 203, 303–311 (1982).
Sandberg et al., Thromb. Res. 18:871 (1980).
Nichols et al., Blood 68 (Suppl. 1): 300a (1986).
Tullis et al., Blood 14:459 (1959).
Chao et al., Thromb. Haem. 47:459 (1982).
Chao et al., Brit. J. Haematol. 39:177 (1978).
Kahn et al., Blood 66:1 (1985).
Hjort et al., Proc. Soc. Exp. Biol. Med. 102:31 (1959).
Firkin et al., Blood 15:388 (1960).
Jackson et al., J. Clin. Invest. 38:1689–1697 (1959).
Zucker, J. Lab. Clin. Med. 109:111 (1987).
Stefanini et al., Clin. Res. Proc. 5:151–152 (1957).
Walsh et al., in Hemostasis and Thrombosis, (1987), p. 689.
George et al., Blood, vol. 68, No. 1 (1986) pp. 307–309.
Schilt, U., Overview of Viruses Relevant to Blood Transfusion, "Virus Inactivation in Plasma Products".
Heimburger, N., and Karges, H. E., Strategies to Produce Virus-Safe Blood Derivates. "Virus Inactivation in Plasma Products".
Piszkiewicz, D., Thomas, W., Lieu, M. Y., Tse, D., and Sarno, L., Virus Inactivation by Heat Treatment of Lyophilized Coagulation Factor Concentrates, "Inactivation in Plasma Products".
Winkelman, L., Feldman, P. A., and Evans, D. R., Severe Heat Treatment of Lyophilised Coagulation Factors, "Virus Inactivation Plasma Products".

Primary Examiner—Jacqueline Stone
Attorney, Agent, or Firm—Wolf, Greenfield & Sacks

[57] ABSTRACT

A heat-treated, viral-inactivated platelet membrane microparticle fraction is provided. The microparticles may be prepared from outdated platelets. The microparticle fraction is substantially free of platelet ghosts and may be used as a pharmaceutical preparation in transfusions.

44 Claims, 3 Drawing Sheets

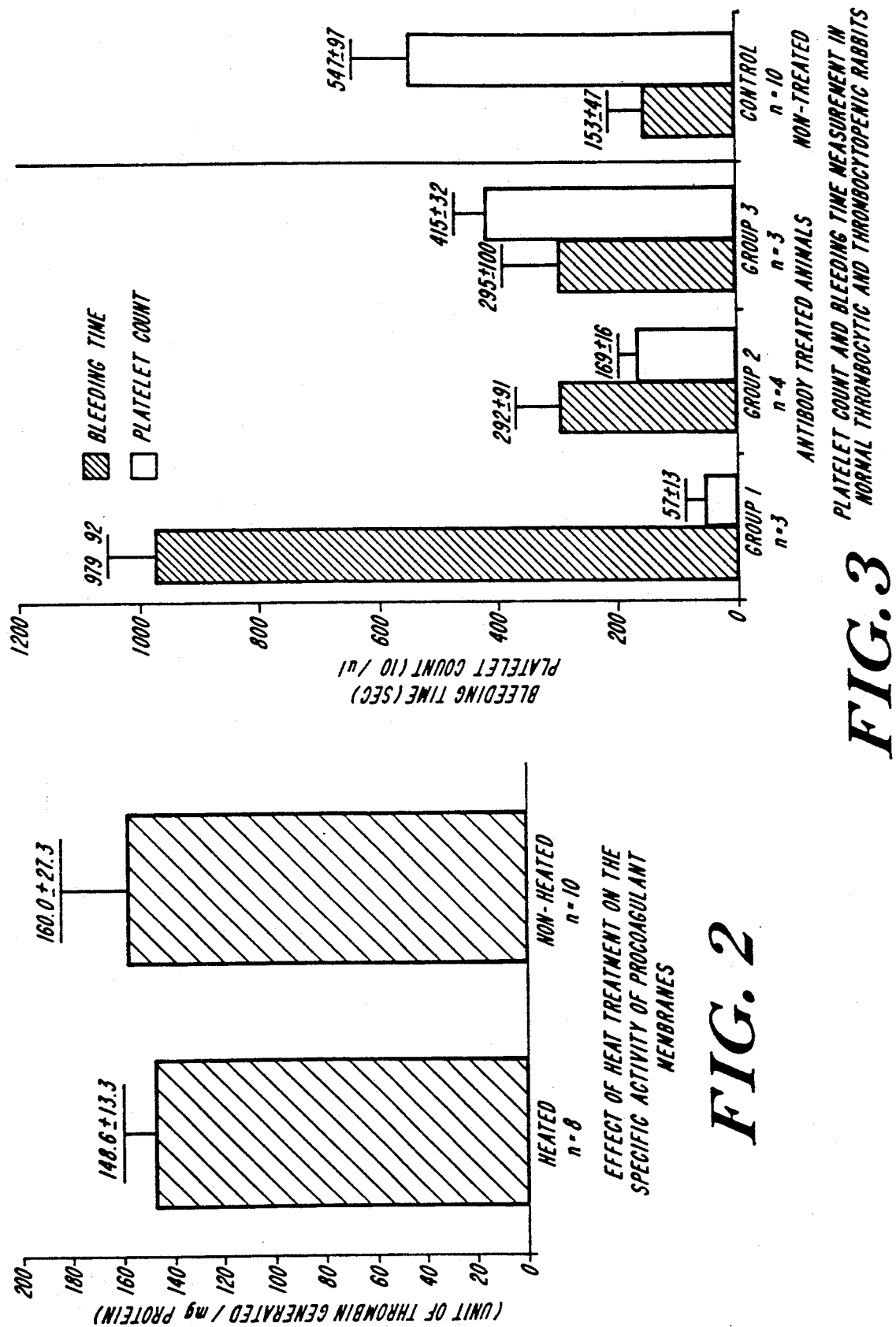

PLATELET MEMBRANE MICROVESICLES

This application is a continuation-in-part of application Ser. No. 07/073,102 filed Jul. 14, 1987, which is a continuation-in-part of Ser. No. 06/623,074, filed Jun. 21, 1984, both now abandoned.

BACKGROUND OF THE INVENTION

This invention relates generally to the field of medicine and more particularly to a platelet membrane microparticle preparation for use in transfusions to control bleeding.

The body of a normal adult contains 4.0 to 5.5 liters of blood, composed of approximately 60% fluid (plasma) and 40% formed elements (red cells; white cells; and platelets). Under normal physiological conditions, the main function of the platelets is prevention of hemorrhage (bleeding).

Platelets are formed in the bone marrow from precursor cells called megakaryocytes and have a life span of 8 to 10 days in circulation. As a consequence of this short life span, platelet deficiency occurs rapidly when the ability of the bone marrow to produce platelets is depressed, such as in cancer patients undergoing chemotherapy. Platelet deficiency also may occur as a result of various diseases when antibodies are produced in vivo against platelet surface glycoproteins or against platelet surface antigens. Such depletion or destruction of platelets results in an insufficient quantity of circulating platelets (a condition referred to as thrombocytopenia) and can cause uncontrolled bleeding. Clinical management of thrombocytopenia has required the transfusion of platelets.

It is predominantly held that only metabolically active platelets can function in vivo to arrest bleeding. As a consequence, transfusion therapy has been dependent on the procurement of high quality, fresh, viable platelets. Platelets for transfusion typically are prepared: (a) from freshly donated blood units, called random-donor platelets or (b) from a single donor by apheresis, called single donor platelets. These transfusion products are plasma suspensions of concentrated, intact platelets.

Several substitutes for intact, viable platelets have been used for transfusion both clinically and in animal models with varying success. In 1956 (1), it was reported that hemostasis was achieved following the clinical administration of lyophilized platelets, suggesting that the morphological integrity of platelets may not be essential for the retention of at least some of the in vivo functions of intact platelets. A major side effect of the intravenous administration of the lyophilized platelet material was that the patient experienced severe pain at the site of infusion, possibly due to vasospasm caused by the high serotonin content in the lyophilized material. Contrary to the foregoing result, it was reported in 1959 (2) that fresh, ultrasound disrupted whole platelet preparations failed to reduce the number of erythrocytes in the lymph of thrombocytopenic dogs. More recently, McGill et al (3) reported that the transfusion of platelet membrane concentrates shortened bleeding times in thrombocytopenic rabbits. The concentrate included ghost platelets about the size of a normal platelet and containing mitochondria and remnants of the surface-connecting system. McGill's concentrate was prepared by: (1) centrifuging the whole blood of rabbits to pellet fresh platelets; (2) freezing the pellet at $-65°$ C.; (3) thawing and then twice-freezing and thawing the pellet; and (4) rinsing and resuspending the pellet in platelet-free plasma.

In preparing the foregoing platelet membrane fractions, temperature conditions of about 4° C. or below were maintained. Such temperatures are standard when working with biologicals as activity is routinely lost in very short intervals when biologicals are exposed to higher temperatures. For example, proteins such as enzymes may be inactivated by heating them to about 60° C. Activity may be lost even at 4° C. For example, it has been reported that partially purified platelet factor 3 (PF-3) loses a major portion of its clotting activity after five days storage at 4° C. (4). (PF-3 appears to be associated with a platelet membrane complex that provides a catalytic surface to promote thrombin generation.) Such loss of activity is of great concern when considering the use of a platelet fraction as a pharmaceutical.

When preparing a platelet fraction for use in humans, it is of course necessary to use sterile conditions. However, even if the platelets are prepared, processed and stored under sterile conditions, the problems of contamination caused by hepatitis, AIDS and other transfusion-related diseases are not obviated.

SUMMARY OF THE INVENTION

The invention provides a platelet membrane microparticle fraction prepared according to a unique method and having unique properties. According to one aspect of the invention, a platelet fraction is heat-treated to reduce or eliminate contamination by hepatitis, AIDS or other transfusion-related diseases. Although it is heat-treated, surprisingly, it retains its procoagulant and hemostatic properties. Moreover, the heat-treated platelet fraction is far more stable than expected, the preparation capable of being stored at 4° C. for at least eight weeks without significant loss of procoagulant activity (greater than 90% retained). It retains this activity (greater than 80%) even after lyophilization.

The platelet membrane microparticle fraction of the invention is substantially free of ghost platelets; it contains relatively homogeneous microparticles. Preferably, at least 80% of the microparticles have a diameter less than 600 nanometers. (95% <1000 nm) Most preferably, the microvesicles have an average diameter of between about 300 and 400 nanometers. Such microparticles are about 1/5 to 1/7 the size of a typical ghost platelet.

The microparticle fraction contains virtually no serotonin (less than 0.02% of that found in platelet lysates), thereby eliminating the respiratory and vascular problems characteristic when certain of the preparations of the prior art are used for transfusion. The preparation also has no detectable purine nucleoside phosphorylase activity, a cytoplasmic enzyme marker. It further is substantially free of factors V, VIII, IX and X, and also is substantially free of GPIIb/IIIa. Preferably the ratio of protein versus phospholipid is $1.97\pm0.10$ (mean $\pm$SD, n=7). In one embodiment the microparticle fraction has 3% carbohydrate, 30% phospholipid, 58% protein and 9% cholesterol by weight.

The platelet membrane microparticle fraction may be prepared by repeated freeze-thawing and washing platelets to yield primarily ghost platelets and a lysate. The ghost platelets then are separated from the lysate and are suspended in a solution to form a suspension. Then the suspension containing the ghost platelets is heated to at least 60° C. for at least two hours to inactivate viral contaminants. The heat treatment also causes a precipitate to form. However, the precipitate is not removed at this point because it contains a significant amount of the desired activity. Instead, the suspension including the precipitate first is homogenized, preferably by sonication, and then the precipitate is separated from the suspension. The suspension then may be stored or used for transfusion.

Surprisingly, the microparticle fraction of the invention may be prepared from outdated platelets. Typically, hospitals and the like store platelets for transfusion at room temperature for three to five days. After this, the platelets are considered unusable and are discarded as "outdated platelets". It has been discovered that the microparticle fraction of the invention may be prepared from such outdated platelets. Such a microparticle fraction has a PF-3 specific activity comparable to that of fresh platelets. Thus, the invention has as one of its objects the provision of a platelet fraction for transfusion prepared wholly or in part from outdated platelets, thereby making use of huge quantities of platelets heretofore discarded as useless.

The platelet membrane microparticle fraction of the invention may be used in a pharmaceutically effective amount in the treatment of animals or humans to prevent bleeding. When used as a pharmaceutical preparation for transfusions, the sterile preparation may be suspended in any physiologically compatible solution such as saline or plasma. It may be used alone, or with other agents, including whole platelets. The preparation is an ideal additive to artificial blood. The preparation also may be applied topically to stop bleeding and to treat wounds. In this regard the preparation may be suspended in a gel or impregnated in a carrier such as gauze. The preparation also may be used as a carrier for drug delivery, or may be labeled and used diagnostically, for example, as an imaging agent to trace the location of a clot.

BRIEF DESCRIPTION OF THE DRAWINGS

FIG. 2 is a graph showing the effect of heat treatment on PF-3, specific activity;

FIG. 3 is a graph showing the platelet count and bleeding time in normal thrombocytic and thrombocytopenic rabbits;

DETAILED DESCRIPTION OF THE DRAWINGS

Figure 1:
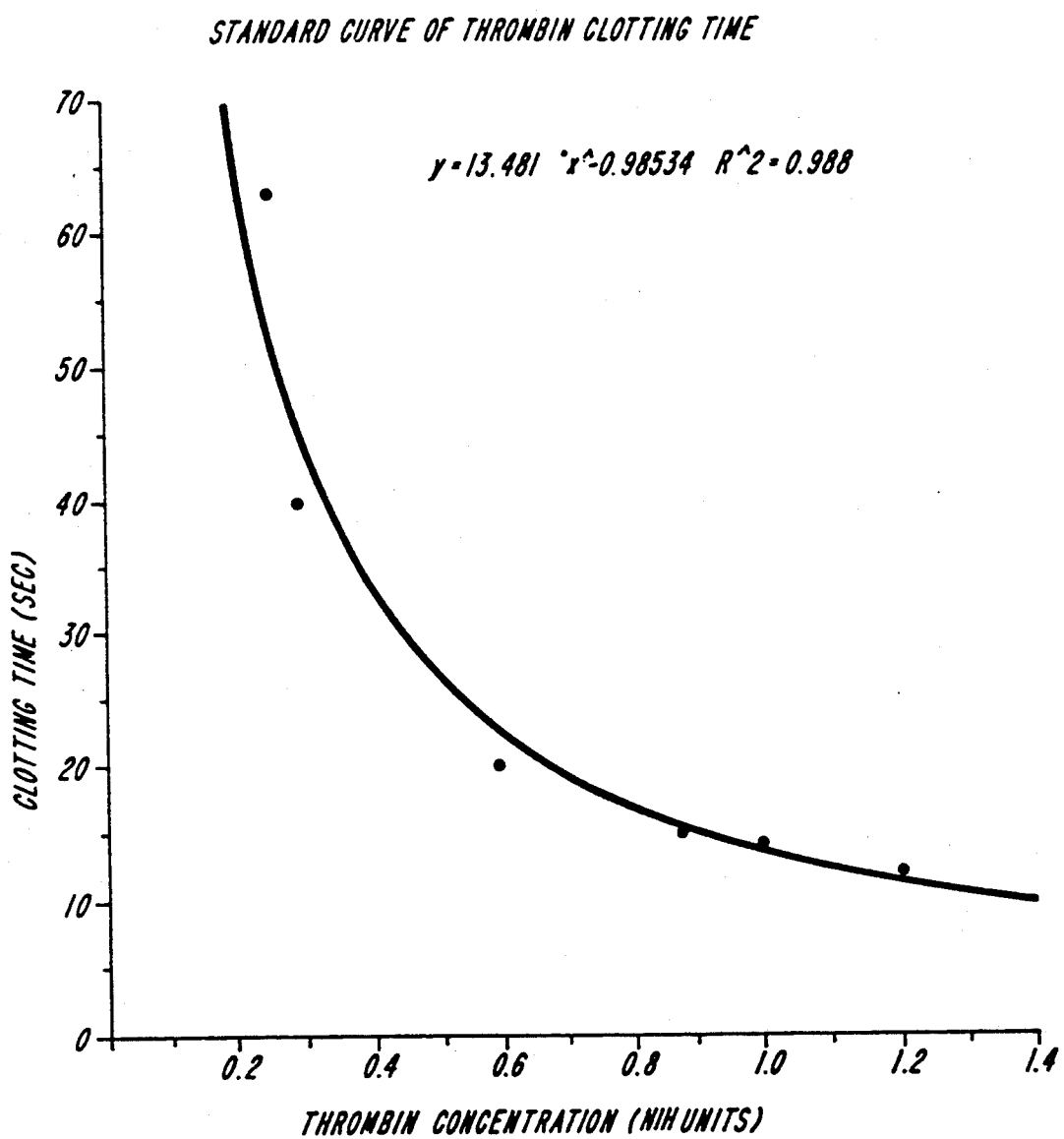
FIG. 1 is a graph showing a standard curve for thrombin clotting time.

Freshly-collected, stored (one to five days at 20°–25° C.) or outdated (beyond five days at 4° C.) platelet concentrates (50–60 ml/concentrate) were pooled in 600 ml blood bags (Fenwall transfer pack unit, 4R2023, Fenwall Laboratories, Deerfield, Ill.) via sterile plasma transfer sets (Fenwall 4C2243, Fenwall Laboratories, supra). Each bag contained a total of 500–600 ml of platelet concentrates (hereinafter, 600 ml unit). The 600 ml units were centrifuged at 1,000 rpm for 11 minutes at 22° C. to remove contaminating red and white blood cells (PR7000, International Equipment Company, Needham Heights, Mass.). The supernatants, which contained the platelets, then were transferred to new 600 ml blood bags and centrifuged at 3,000 rpm for 25 minutes at 22° C. to separate platelets from plasma. Platelet-poor plasma was expressed and each of the resulting platelet pellets was gently resuspended in 20 ml of an 0.9% NaCl solution (physiological saline), diluted to a final volume of 100 ml with additional saline, and then pooled in 300 ml blood bags (three 100 ml samples per bag corresponding to three original 600 ml units). The resuspended platelets again were pelleted by centrifugation at 3,000 rpm for 20 minutes at 22° C. The supernatant was removed and the platelet pellet was washed twice with physiological saline by repeated resuspension and centrifugation.

The washed platelets were finally resuspended in physiological saline (25 ml per each 600 ml unit) and disrupted by repeated freezing (at $-80°$ C. for at least six hours) and thawing (at 25° C. for at least one hour), three times. The frozen and thawed suspension was diluted with physiological saline (100 ml per each 600 ml unit) and centrifuged at 3,000 rpm for 30 minutes to collect a platelet ghost pellet. This platelet ghost pellet was resuspended in physiological saline (100 ml per each 600 ml unit) and washed twice by repeated resuspension and centrifugation.

Other methods may be employed to disrupt platelet membranes and to isolate a platelet ghost fraction. For example, platelets may be equilibrated with glycerol and then may be broken hypotonically by rapid dilution of the glycerol concentration external to the cell. This creates an osmotic pressure gradient across the external membrane of the platelets, which leads to a rupture of the cell membrane. In addition, many other chemical agents (e.g., NaCl) may be used in a similar manner to induce osmotic shock and disrupt platelets. According to the preferred embodiment, repeated freezing and thawing was used.

The washed ghost pellet was resuspended in physiological saline (40–50 ml per each 600 ml unit) and heated at 60° C. for 20 hours in a water bath. Alternatively, the platelet ghost suspension may be heated to 100° C. for five minutes. These conditions are sufficient to inactivate any viral contaminants. A gross precipitate developed during the heat treatment. This heat-treated, platelet ghost suspension then was homogenized in a sonicator (ultrasonic processor Model W-385, Heat Systems, Inc., Farmingdale, N.Y.) using a ½" disruptor horn in a flow cell (Model 800B, Heat Systems). The sonicator system was flushed first with nitrogen prior to injection of the platelet ghost suspension. The suspension was sonicated by pulsing at 20 kHz for 5 minutes and 43 seconds (2 second cycle, 1.4 seconds on, 0.6 seconds off) with output control setting at "4" to produce double amplitude of 48 micrometers. The sonicated preparation next was centrifuged at 3,000 rpm for 30 minutes at 22° C. to separate the precipitated material from the formed platelet membrane microparticles which remain in the supernatant. The supernatant was removed and stored in sealed containers at either 4° C., $-20°$ C. or $-80°$ C. under nitrogen, or stored lyophilized under nitrogen. Unless otherwise indicated, microparticles stored at 4° C. were used in the following procedures.

The platelet microparticle fraction prepared according to the foregoing procedure was substantially free of platelet ghosts, with greater than 80% of the microparticles being less than 600 nanometers in diameter and greater than 95% less than 1,000 nanometers. The average diameter of the microparticles prepared from newly outdated platelets (within two weeks after outdating) for 7 different preparations was between 300 and 400 nanometers. The mean diameter for the 7 preparations was 341 nanometers.

The platelet microparticle fraction also was substantially free of serotonin, purine nucleoside phosphorylase, coagulation factors V, VIII, IX and X, GPIIb/IIIa (a surface glycoprotein) and thrombospondin (an alpha granule component). On the other hand, GPIb (another surface glycoprotein) was present and Beta-glucuronidase (a lyzosomal marker) also was detectable (about 25% as a percent of lysate).

The composition of the platelet microparticle fraction was determined for certain components and is presented in Table I below:

TABLE I

| | PERCENT OF COMBINED WEIGHT (W/W) | | | |
|---|---|---|---|---|
| EXPT. | CARBO-HYDRATE | PHOSPHO-LIPID | PRO-TEIN | CHOLES-TEROL (Assumed) |
| 1 | 3.2 | 30.8 | 57.0 | 9% |
| 2 | 3.2 | 29.2 | 58.6 | 9% |
| 3 | 3.5 | 30.8 | 56.9 | 9% |
| 4 | 3.3 | 29.3 | 58.5 | 9% |
| | 3.3 ± 0.14 | 30. ± 0.9 | 57.8 ± 0.9 | 9% |

The procoagulant activity of the preferred platelet microparticle fraction prepared from newly outdated platelets was determined using the Russel's viper venom time (5) which is used to measure PF-3 activity. The Russel assay is a thrombin generation test, for which the end point may be determined by fibrinogen clotting. The specific activity was determined by comparison to a thrombin standard curve and may be expressed as units (U) of thrombin generated per mg of platelet protein or per mg of platelet phospholipid. The PF-3 specific activity per mg protein (U/mg) was determined to be 148.1±13.4 (mean ±SD; n=7). The PF-3 specific activity per mg phospholipid (U/mg) was determined to be 291.3±40.0 (n=7). The specific activity was retained even after lyophilization, although it was necessary to add a protective material to the microparticle fraction to retain greater than about 60% of the specific activity (sucrose at 0.4 gm/dl, >90% activity retained.)

The composition of the phospholipid portion was determined and is shown in Table II:

TABLE II

| | PERCENT OF COMBINED PHOSPHOLIPID (W/W) | | | | |
|---|---|---|---|---|---|
| EXP. | PI | PS | PE | PC | SP |
| 1 | 5.9 | 10.8 | 21.6 | 47.6 | 14.3 |
| 2 | 6.8 | 10.7 | 20.6 | 41.8 | 15.4 |
| 3 | 6.2 | 10.1 | 23.9 | 43.1 | 17.7 |
| 4 | 4.4 | 8.8 | 22.9 | 50.5 | 14.1 |
| | 5.8 ± 1.0 | 10.1 ± 0.9 | 22.5 ± 1.5 | 45.8 ± 4.0 | 15.4 ± 1.7 |

PI: phosphatidylinositol
PS: phosphatidylserine
PE: phosphatidylethanolamine
PC: phosphatidylcholine
SP: sphingomyelin Platelet microparticle fractions were tested for their procoagulant activity and for their ability to control bleeding in thrombocytopenic animals. The procoagulant activity of a microparticle fraction prepared from newly outdated platelets was found to be comparable to one prepared from fresh platelets. Fractions prepared from fresh and newly outdated platelets had comparable procoagulant activity to whole platelets. The transfusion of this fraction shortened bleeding time in all recipient animals.

The effect of heat treatment and the effect of sonication on procoagulant activity also was tested. The microparticle fraction prepared from newly outdated platelets was found to be relatively stable to heat treatment. It further was discovered that the procoagulant activity of this platelet microparticle fraction was diminished greatly when homogenization preceded heat treatment. These and other properties of the microparticle fractions of the invention are set forth more fully in the examples below.

The foregoing description is of a preferred embodiment. The invention in its broadest sense, however, is not so limited. One aspect of the invention is the provision of platelets or a platelet membrane fraction heat-treated to eliminate viral contaminants. While such heat treatment is known to inactivate viral contaminants generally, it never has been used in connection with a platelet preparation. The invention therefore provides for the first time a viral-inactivated, platelet fraction useful for transfusion.

Another aspect of the invention is a transfusion preparation which has been prepared from outdated platelets. The invention for the very first time makes the great quantities of outdated platelets, ordinarily discarded, useful for transfusion. Moreover, because there is an increasing potential for viral contamination of outdated platelets during storage, the heat treatment step of the invention also contributes to making outdated platelets useful by ensuring that they are viral-inactivated.

The invention also combines heat-inactivation with a homogenization step in preparing a platelet microparticle fraction substantially free of ghost platelets. The preparation contains microparticles of homogeneous size and substantially free of unwanted cytoplasmic material. According to a preferred method of the invention, the homogenization (sonication) follows the heat-inactivation step which results both in creating the microparticles of homogeneous size and in preventing a substantial amount of the activity from being bound up in any precipitate formed during the heat-inactivation step.

As described above, the microparticle fraction may be prepared in stages. First, the platelet membrane was partially disrupted to form a ghost platelet fraction and a lysate containing cytoplasmic materials. Once the platelet ghosts are separated from this cytoplasmic material, then the ghost platelets are homogenized to form a fraction substantially free of ghost platelets and containing microparticles of substantially uniform size. It will be understood, however, that the preliminary stage of partial disruption may be eliminated altogether. Thus, platelets may be sonicated and the formed microparticles may be isolated from the lysate.

It is believed that the platelet membrane microparticle fraction of the invention is substantially non-antigenic when compared to whole platelets and therefore may be prepared from pooled platelets collected from various donors with matching blood groups.

EXAMPLE 1

PF-3 (platelet factor-3) procoagulant activity was measured by the Russel viper venom time assay, which is a thrombin generation test. The end point of the test is determined visually by the clotting of fibrinogen present in a pooled human plasma sample.

A stock solution of $CaCl_2$ (0.025M in imidazol buffer, pH 7.3) was maintained at 37° C. Pooled human plasma and the platelet membrane micorparticle fractions in solution (25 ug/ml in saline) were stored at room temperature. Russel viper venom (RVV; 10 ug/ml in saline; Wellcome Diagnostics, Dartford, England) was kept on ice.

The assay was initiated by mixing and incubating 0.1 ml each of pooled plasma and the solution of platelet membrane microparticles in a borosilicate glass tube (12×75 mm) at 37° C. for 5–10 minutes. RVV solution (0.1 ml) was then added and further incubated for 30 seconds at 37° C. followed by adding 0.1 ml of $CaCl_2$ solution. The time between the addition of $CaCl_2$ solution and the detection of fibrin clotting was determined. The unit of thrombin generated by the assay system was calculated from a standard curve of thrombin clotting time (FIG. 1) using purified bovine thrombin (Sigma 850-1; Sigma Chemical Co., St. Louis, Mo.) and pooled human plasma.

The effect of heat treatment and the effect of sonication on procoagulant activity (PF-3) using Russel's viper venom time (5) was tested. As illustrated in FIG. 2, heat treatment, followed by sonication, resulted in a platelet membrane microparticle fraction that retained a substantial amount of its procoagulant activity. However, when sonication preceded heat treatment (not shown), the procoagulant activity of the platelet membrane microparticle fraction was altered drastically, the procoagulant activity being reduced by 50%.

EXAMPLE 2

The platelet microparticles were tested for their ability to control bleeding in antibody-induced, thrombocytopenic animals. Anti-rabbit platelet antiserum was used to induce thrombocytopenia in rabbits. Platelet counts and bleeding time first were determined in 10 normal rabbits (body weight 3.53±0.41 Kg; platelet count, 548,000±97,000/ul; bleeding time, 153±47 sec; mean±SD). Anti rabbit platelet antiserum was obtained from a commercial source then was administered intravenously to the 10 rabbits at a dose of 0.2–0.4 ml antiserum per kg body weight. At two hours after antiserum injection, thrombo-cytopenia of varying degree was present in all animals. Data were grouped according to the degree of "induced thrombocytopenia": GROUP 1, platelet count less than 80,000/ul; GROUP 2, platelet count between 100,000–200,000/ul and GROUP 3, platelet count above 200,000/ul (FIG. 3).

Prolongation of bleeding time also was induced in all 10 antiserum treated rabbits (measured at two hours after antiserum injection). Marked prolongation occurred only in Group 1 animals (severe thrombocytopenia, <75,000/ul) and a moderate prolongation was observed in both Group 2 and 3 animals (FIG. 3).

Figure 4:
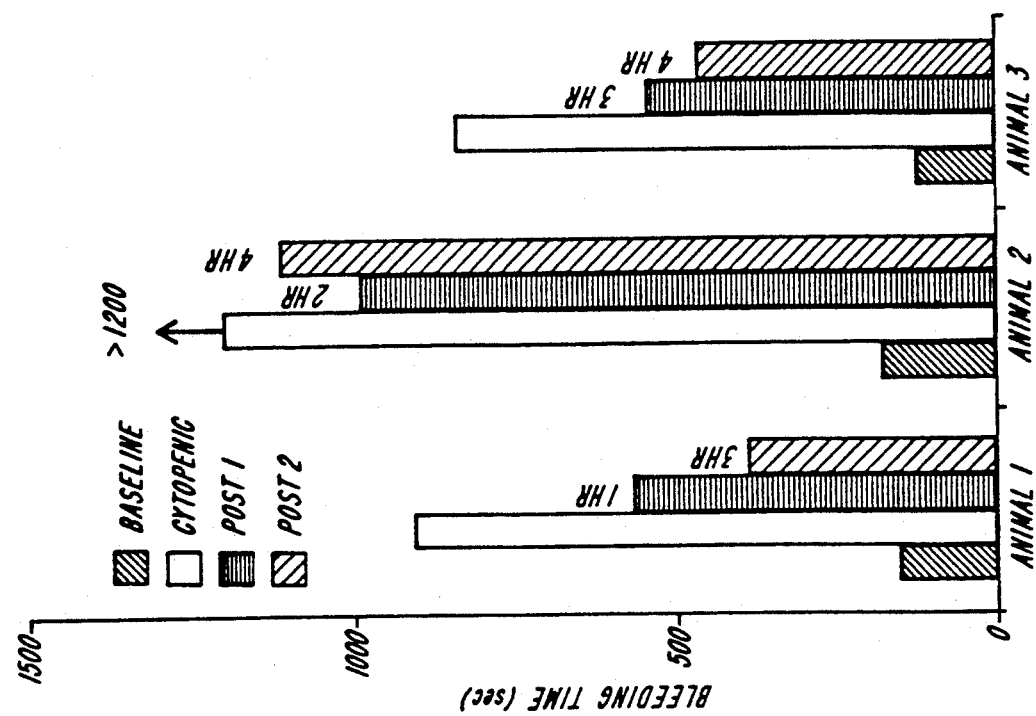
FIG. 4 is a graph showing the effect of transfused platelet membrane microparticles on antibody induced thrombocytopenic animals.

Platelet microparticle fractions prepared from newly outdated platelets were transfused (2 mg protein/kg body weight) into Group 1 animals with severe thrombocytopenia. Referring to FIG. 4, platelet counts obtained at two hours after antiserum injection were 41,000, 73,000 and 56,000/ul for animals 1, 2 and 3, respectively. At the same interval, bleeding time was marked prolonged in all three rabbits, especially rabbit number 2, in which profuse bleeding from the test site persisted even at 20 minutes after the initial incision and required application of local pressure to stop the bleeding. After receiving the platelet microparticles, animals 1 and 3 showed progressive shortening of bleeding time, while spontaneous arrest of bleeding occurred within 20 minutes in rabbit number 2, without the need of local pressure. Thus, a general trend of shortening of bleeding time after transfusion of the platelet microparticles of the invention was demonstrated in all recipient animals.

EXAMPLE 3

The platelet microparticles were tested for their ability to control bleeding in Doxorubicin hydrochloride-induced, thrombocytopenic animals. Doxorubicin hydrochloride (Adriamycin; 2 mg/kg body weight) was administered intravenously to nine rabbits to induce thrombocytopenia. The baseline platelet count (before doxorubicin injection) was 488,000±94,000/ul. The baseline bleeding time was 128±21 sec. One week after doxorubicin injection, platelet count was reduced to 130,000±31,000/ul ($p<0.01$) with a 2.4 fold increase in bleeding time (311±89 sec; n=9) over the thrombocytopenic controls ($p<0.01$).

Figure 5:
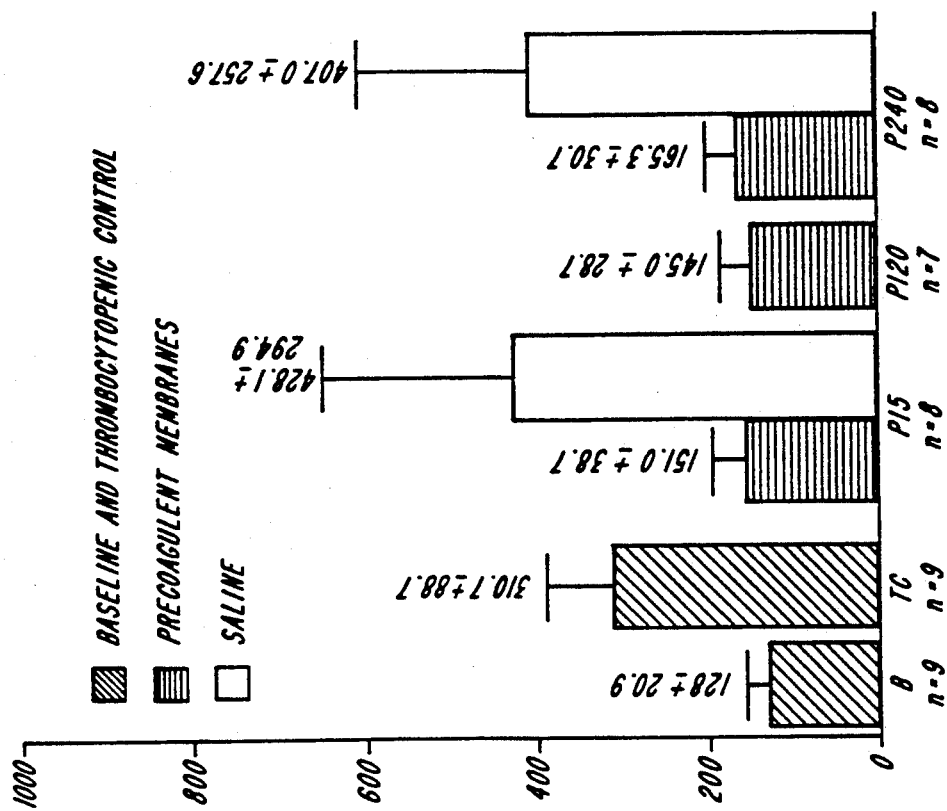
FIG. 5 is a graph showing the effect of transfused platelet membrane microparticles on the bleeding time in doxorubicin hydrochloride-induced thrombocytopenic animals.

Platelet microparticle fractions (2 mg membrane protein/Kg body weight), prepared from newly outdated platelets or saline preparations were transfused into the thrombocytopenic rabbits induced by doxorubicin. Hemostatic efficacy was demonstrated in all animals that received procoagulant membranes. Repeat measurements of bleeding time at 15 minutes, two and four hours post-transfusion showed a significant shortening of bleeding time from thrombocytopenic controls (<0.01) (FIG. 5). In contrast, no significant differences were noted between measurements obtained before and after infusion of saline to thrombocytopenic rabbits.

The foregoing transfusion studies in thrombocytopenic rabbits demonstrate the hemostatic efficacy of platelet procoagulant membranes.

It will be understood by those skilled in the art that various changes and modifications to the embodiments shown in the drawings and described above may be made within the scope of the invention, It, therefore, is intended that all matter contained in the above description and shown in the accompanying drawings shall be interpreted in an illustrative and not limiting sense.

REFERENCES

1) Klein, E., Farber, S., Djersasi, I., Toch, R., Freeman, G., Arnold, P., "The Preparation and Clinical Administration of Lyophilized Platelet Material to Children with Acute Leukemia and Aplastic Anemia", *J. Pediatrics*, 49:517, 1956.
2) Hjort, P., Perman, V., and Cronkite, E., "Fresh, Disintegrated Platelets and Radiation Thrombocytopenia: Correction of Prothrombin Consumption without Correction of Bleeding".
3) McGill, M., Fugman, D., Vittorio, N., and Darrow, C., "Platelet Membrane Vesicles Reduced Microvascular Bleeding Times in Thrombocytopenic Rabbits", *J. Lab. Clin. Med*, 109:127–133, 1987.
4) Wu, V-Y., McCoy, L. E., "Platelet Factor 3: Quantitation and Characterization", *Thromb. Res.*, 11:581–593, 1977.
5) Spaet, T. H., Cintron, J., "Studies on Platelet Factor-3 Availability", *Brit. J. Hamematol*, 11:269, 1965.

What is claimed is:

1. A method for preparing a platelet membrane fraction for transfusion comprising heating platelets or a membrane fraction thereof to at least 60° C. and isolating the heat-treated membrane fraction.

2. A method as claimed in claim 1 further comprising sonicating said platelets or membrane fraction thereof after heating to form a platelet membrane microparticle fraction substantially free of ghost platelets.

3. A method as claimed in claim 1 further comprising,
first suspending said platelets or membrane fraction thereof in a solution to form a suspension,
heating said suspension to at least 60° C.,
homogenizing said suspension, and
separating any precipitate formed as a result of heating from said suspension.

4. A method as claimed in claim 3 wherein said suspension is homogenized by sonication.

5. A method as claimed in claim 1 further comprising,
first forming a ghost platelet fraction and a lysate from platelets,
separating said ghost platelet fraction from said lysate, and
then heating said ghost platelet fraction to at least 60° C.

6. A method as claim in claim 5 further comprising,
further homogenizing said ghost platelet fraction to form a microparticle fraction substantially free of ghost platelets.

7. A method as claimed in claim 6 further comprising,
suspending said ghost platelet fraction in a solution to form a suspension prior to heating,
heating said suspension to at least 60° C.,
sonicating said suspension to form a microparticle fraction substantially free of ghost platelets, and
separating any precipitate formed during heating from said microparticle fraction.

8. A method as claimed in claim 5 wherein said platelets are freeze thawed to form said ghost platelet fraction and said lysate.

9. A method as claimed in claim 1 further comprising,
sonicating said platelets or platelet membrane fraction thereof after heating to form a microparticle fraction substantially free of ghosts, and
separating any precipitate formed as a result of said heating from said microparticle fraction.

10. A method as claimed in claim 1 further comprising,
removing substantially all of any serotonin from said platelets or membrane fraction thereof.

11. A method as claimed in claim 1 further comprising disrupting the membrane of whole platelets to form a lysate and a membrane fraction and separating said lysate from said membrane fraction.

12. A method as claimed in claims 1, 2, 3, 9 or 11 further comprising heating outdated platelets or a fraction thereof to at least 60° C.

13. A method for preparing a therapeutic preparation of platelet microparticle fraction comprising disrupting the membranes of outdated platelets to form a platelet microparticle fraction substantially free of ghost platelets.

14. A method as claimed in claim 13 further characterized by separating substantially all of the cytoplasmic serotonin from the microparticle fraction.

15. A method as claimed in claim 13 further comprising,
disrupting the membranes of the outdated platelets to form a ghost fraction and a lysate,
separating said ghost fraction and said lysate, and
then sonicating said ghost fraction to form the microparticle fraction.

16. A method as claimed in claim 15 further comprising,
forming the ghost fraction by freeze thawing outdated platelets.

17. A method as claimed in claim 15 further comprising,
heating said ghost fraction to at least 60° C. prior to sonicating said ghost fraction.

18. A method as claimed in claim 17 wherein the outdated platelets comprise a mixture of outdated platelets obtained from more than one person.

19. A method for preparing platelets for use in transfusion comprising,
homogenizing said platelets to form a platelet microparticle fraction substantially free of ghost platelets,
separating the microparticle fraction from substantially all of any serotinin released from the whole platelets, and
isolating the microparticle fraction.

20. A method for preparing platelets for use in transfusion comprising,
freeze thawing platelets to yield a platelet ghost fraction and a lysate,
separating the ghost platelet fraction from the lysate,
suspending the ghost platelet fraction in a solution to form a suspension,
sonicating the ghost platelet fraction to form a microparticle fraction substantially free of ghost platelets, and
isolating the microparticle fraction.

21. A method for inhibiting bleeding in a mammal comprising administering to a mammal a pharmaceutically-effective amount of a platelet fraction prepared from outdated platelets.

22. A method as claimed in claim 21 wherein said fraction is administered topically.

23. A method as claimed in claim 21 further comprising heating said outdated platelets or fraction thereof to at least 60° C. prior to administering said fraction.

24. A method as claimed in claim 21 wherein a microparticle platelet fraction substantially free of ghost platelets is administered.

25. A method for inhibiting bleeding in a mammal comprising,
administering to a mammal a pharmaceutically-effective amount of a transfusion material prepared by heating platelets or a membrane fraction thereof to at least 60° C. and then isolating the heat-treated membrane fraction.

26. A method for inhibiting bleeding in a mammal comprising,
administering a pharmaceutically-effective amount of a microparticle fraction to a mammal, the microparticle fraction prepared by homogenizing platelets or a fraction thereof to form a platelet microparticle fraction substantially free of ghost platelets,
separating the microparticle fraction from substantially all of any serotinin released during said homogenization step, and
isolating the microparticle fraction.

27. An isolated platelet membrane microparticle fraction substantially free of platelets, platelet ghosts and virus.

28. A platelet membrane microparticle fraction as claimed in claim 27 being substantially free of cytoplasmic serotonin.

29. A platelet membrane microparticle fraction as claimed in claim 27 having about 3% carbohydrate, 30% phospholipid, 58% protein, and 9% cholesterol as a percentage of total weight.

30. A platelet membrane microparticle fraction as claimed in claim 27 wherein 80% of the microvesicles are under 600 nanometers in diameter.

31. A platelet membrane microparticle fraction as claimed in claim 27 wherein the microvesicles have an average diameter of between about 300 nanometers and 400 nanometers.

32. A platelet membrane microparticle fraction as claimed in claim 27, further characterized in being substantially free of Factors V, VIII, IX and X, of Purine nucleoside phosphorylase, and of GPIIb/IIIa.

33. A pharmaceutical preparation containing a pharmaceutically-effective amount of the microparticle fraction of claim 27.

34. A pharmaceutical preparation containing a pharmaceutically-effective amount of the microparticle fraction of claim 28.

35. A pharmaceutical preparation containing a pharmaceutically-effective amount of the microparticle fraction of claim 29.

36. A pharmaceutical preparation containing a pharmaceutically-effective amount of the microparticle fraction of claim 30.

37. A pharmaceutical preparation containing a pharmaceutically-effective amount of the microparticle fraction of claim 31.

38. A method for preparing a platelet membrane fraction as claimed in claim 1 wherein a heat-treated membrane fraction having procoagulant and hemostatic properties is isolated.

39. A method for preparing a platelet membrane fraction as claimed in claim 1 wherein a heat-treated membrane fraction capable of achieving hemostasis when introduced into a bleeding mammal is isolated.

40. A method for preparing a platelet membrane fraction as claimed in claim 1 wherein a heat-treated membrane fraction having a protein:phospholipid content of about 2:1 is isolated.

41. A method for preparing a platelet membrane fraction as claimed in claim 1 wherein a heat-treated membrane fraction having a protein:phospholipid content of less than 2:1 is isolated.

42. A method for preparing a platelet membrane fraction as claimed in claim 1 wherein a heat-treated membrane fraction having GPIb activity and substantially free of GPIIb-IIIa and substantially free of plasma proteins is isolated.

43. A platelet membrane microparticle fraction as claimed in claim 27 wherein the fraction has a protein:phospholipid ratio of about 2:1.

44. A platelet membrane microparticle fraction as claimed in claim 17 wherein the fraction has a protein:phospholipid ratio of less than 2:1.

* * * * *